United States Patent
Travers et al.

(10) Patent No.: US 7,098,370 B2
(45) Date of Patent: Aug. 29, 2006

(54) PROCESS FOR THE PRODUCTION OF PHENYLALKANES USING A CATALYST THAT CONTAINS AT LEAST ONE HETEROPOLYACID

(75) Inventors: Christine Travers, Rueil Malmaison (FR); Jean-Fransois Joly, Lyons (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 327 days.

(21) Appl. No.: 10/214,431

(22) Filed: Aug. 8, 2002

(65) Prior Publication Data
US 2003/0040653 A1 Feb. 27, 2003

(30) Foreign Application Priority Data
Aug. 8, 2001 (FR) .................................. 01 10622

(51) Int. Cl.
*C07C 2/70* (2006.01)
(52) U.S. Cl. ........................ 585/466; 585/455; 585/323
(58) Field of Classification Search ................ 585/323, 585/455, 466
See application file for complete search history.

(56) References Cited

U.S. PATENT DOCUMENTS 5,919,725 A * 7/1999 Soled et al. ................ 502/210
5,955,642 A * 9/1999 Merrill et al. .............. 585/323

FOREIGN PATENT DOCUMENTS

WO  95 13869 WO   5/1995

OTHER PUBLICATIONS

XP-002194819 & CN 1 277 894 A (Dalian Chem & Physical Inst Chinese Acad), Dec. 27, 2000 (Dec. 27, 1000).

* cited by examiner

*Primary Examiner*—Thuan D Dang
(74) *Attorney, Agent, or Firm*—Millen, White, Zelano & Branigan, P.C.

(57) ABSTRACT

The invention relates to a process for the production of a mixture of compounds that comprises for the most part at least one mono-alkylbenzene that belongs to the group that is formed by the 2-, 3-, 4-, 5- and 6-phenylalkanes by alkylation of benzene with at least one monoolefin that comprises at least two carbon atoms in its molecule, in the presence of a catalyst that comprises 12-tungstophosphoric acid and/or 12-tungstomolybdic acid, deposited on a substrate that develops a large specific surface area and a high pore volume and that comprises a majority proportion of zirconium oxide ($ZrO_2$).

21 Claims, No Drawings

PROCESS FOR THE PRODUCTION OF PHENYLALKANES USING A CATALYST THAT CONTAINS AT LEAST ONE HETEROPOLYACID

TECHNICAL FIELD

This invention relates to the field of the processes for the production of phenylalkanes by alkylation of benzene with at least one monoolefin that comprises at least two carbon atoms in its molecule in the presence of at least one catalyst that contains 12-tungstophosphoric acid and/or 12-tungstomolybdic acid that is deposited on a substrate that develops a large specific surface area and a high pore volume, comprising a majority proportion of zirconium oxide (ZrO2). Most often, at least one linear or branched olefin is used that comprises less than 30 carbon atoms in its molecule. The olefin that is used often comprises 9 to 16 carbon atoms in its molecule, and more particularly 10 to 14 carbon atoms in its molecule. This olefin is preferably a linear olefin. For example, a hydrocarbon fraction that comprises at least one olefin is used.

PRIOR ART

The phenylalkanes that are obtained according to the invention constitute, for some of them, compounds for the formulation, after sulfonation, of biodegradable detergents. Currently, the bases for biodegradable detergents rely extensively on linear alkylbenzenes. The production of this type of compounds increases regularly. One of the main properties that is desired for these compounds, after the sulfonation stage, is, in addition to their capacity as detergent, their biodegradability. To ensure maximum biodegradability, the alkyl group should be linear and long, and the distance between the sulfonate group and the terminal carbon of the linear chain should be maximum. In this framework, the most advantageous agents for alkylating benzene comprise the linear olefins of C9–C16, and preferably C10–C14.

The linear alkylbenzenes (LAB, linear alkylbenzene according to the English initials of the name of these products) that are obtained by alkylation of benzene with linear olefin(s) are prepared today by two main processes. The first major type of process uses, during the stage of alkylating benzene, hydrofluoric acid HF as an acidic catalyst. The second type of process uses a Friedel-Crafts-type catalyst, in particular with a base of AlCl$_3$. These two processes lead to the formation of 2-, 3-, 4-, 5- and 6-phenylalkanes. The primary drawback of these processes is linked to environmental constraints. The process that relies on the use of hydrofluoric acid poses severe safety problems, on the one hand, and retreatment of waste, on the other hand. The processes that are based on the use of Friedel-Crafts-type catalysts pose the problem of waste: actually, for this type of process, it is necessary to neutralize the effluents by a basic solution at the outlet of the reactor. For the two processes, the problems that are linked to the separation of catalyst from the reaction products are added to these various drawbacks.

These various constraints explain the advantage that there is in developing a process for alkylating benzene by the olefins and more particularly by linear olefins with long chains in the presence of a solid catalyst.

The prior art essentially notes the use of catalysts that have geometric selectivity properties and lead to an improved selectivity of 2- and 3-phenylalkanes. Said catalysts that have geometric selectivity properties consist of zeolites. Thus, Patent U.S. Pat. No. 4,301,317 describes an entire series of zeolites including: cancrinite, gmelinite, mordenite, offretite and ZSM-12. These zeolites are, in particular, characterized in that their pore opening is between about 6 and about 7 angstroms (Å) in diameter (1 Å=10$^{-10}$ m).

In Patent FR-B-2,697,246 that is filed by the applicant, it is shown that it is possible to use catalysts based on dealuminified Y zeolite. These Y zeolites have a pore opening of close to 7.4 Å. Concerning the use of Y zeolites, Patent EP-B1-160,144 describes the use of partially crystallized zeolites, in particular Y zeolites that have a crystallinity of between 30 and 80%, and Patent U.S. Pat. No. 5,036,033 describes the use of Y zeolites that are rich in ammonium cations. In another patent application that was filed by the applicant and published under number FR-A-2, 795,402, it is shown that it is possible to use catalysts based on EUO-structural-type zeolites.

For the reaction of alkylation of aromatic compounds by olefins, the use of catalysts based on heteropolyacid salts deposited on porous substrates (such as, for example, MCM-41-type solids) was the subject of several patents, including U.S. Pat. No. 5,366,945 in particular. U.S. Pat. No. 5,919, 725 and International Patent Application WO95/13869 make reference to the deposition of heteropolyacid salts or acid salts on crystalline porous solids. These patents relate in a very general way to all of the possible reactions for alkylating aromatic compounds by the olefins. Patent U.S. Pat. No. 5,919,725 mentions that silica is the preferred substrate for the catalyst.

Furthermore, Patent U.S. Pat. No. 5,866,739 uses salt-based or acid salt-based catalysts, such as those of 12-tungstophosphoric acid or of 12-tungstomolybdic acid, deposited on porous solids. According to the teaching of this patent, the preferred substrate is silica. The analysis of the examples, none of which relates to the alkylation of benzene by an olefin that comprises fewer than 30 carbon atoms in its molecule, confirms that silica is the substrate that provides the most active catalyst.

SUMMARY

This invention relates to a process for the production of a mixture of compounds that comprises for the most part at least one mono-alkylbenzene that belongs to the group that is formed by the 2-, 3-, 4-, 5- and 6-phenylalkanes by alkylating benzene with at least one monoolefin that comprises at least two carbon atoms in its molecule, in the presence of a catalyst that comprises 12-tungstophosphoric acid and/or 12-tungstomolybdic acid, deposited on a substrate comprising a majority proportion of zirconium oxide (ZrO$_2$) which preferably develops a large specific surface area and a high pore volume. The invention relates most particularly to the alkylation of benzene by means of a linear olefin, so as to produce linear phenylalkanes.

ADVANTAGE

It was discovered in a surprising way that the use of catalysts that are defined in a general manner by the fact that they comprise 12-tungstophosphoric acid and/or 12-tungstomolybdic acid, but preferably 12-tungstophosphoric acid, used as such, and not in the form of salts or acid salts of these compounds, deposited on substrates that develop a large specific surface area and a high pore volume comprising a majority proportion of zirconium oxide (ZrO$_2$) exhibit, by alkylating benzene with at least one olefin, catalytic performance levels that are superior to those of catalysts that are described in the prior art. These new catalysts are in particular both very active and very resistant to deactivation.

DESCRIPTION

Within the scope of this invention, the hydrocarbon feedstock, containing benzene, used for carrying out the alkylation of the benzene core, can contain, in addition to a monoolefin, one or more paraffins, one or more other aromatic compound(s), one or more polyolefinic compound(s) (for example diolefinic), or one or more mono-unsaturated and/or poly-unsaturated non-linear olefin(s). These fractions can also contain one or more alpha-olefin(s) in a very variable amount from trace state up to very large amounts, and even for the most part majority amounts relative to said feedstock. It is usually preferred to use feedstocks that contain no or very small amounts of polyolefinic compounds, poly-unsaturated olefin(s) and aromatic compound(s) other than benzene.

The process according to this invention consists in the production, preferably simultaneously, of 2-, 3-, 4-, 5- and 6-phenylalkanes. In the case where the feedstock comprises linear monoolefins, the process according to the invention makes it possible to produce in large part linear phenylalkanes (LAB, linear alkylbenzene according to the English initials of the name of these products). It is also possible to use a feedstock that comprises branched olefins, which then lead to the majority formation of branched phenylalkanes. According to this invention, it is preferred to use linear monoolefins and thus to obtain linear phenylalkanes.

According to a preferred variant of the process of the invention, benzene is reacted in an alkylation reaction zone with a feedstock that contains at least one linear monoolefin that comprises 9 to 16 carbon atoms in its molecule, preferably 10 to 14 carbon atoms in its molecule, upon contact with a catalyst that comprises 12-tungstophosphoric acid and/or 12-tungstomolybdic acid, deposited on a substrate that develops a large specific surface area and a high pore volume comprising a majority proportion of zirconium oxide ($ZrO_2$).

The catalyst that is used in this invention is shaped, for example, in the form of balls or extrudates. It has a good mechanical resistance, preferably such that the bed crushing value, determined according to the Shell method (SMS 1471-74) and characterizing its mechanical resistance, is higher than about 0.7 MPa.

According to a particular and often preferred embodiment of the invention, the substrate of the catalyst comprises a majority proportion of the zirconium oxide and a minority proportion of at least one binder. Within the meaning of this description, the term majority should be understood as defining a proportion by weight of zirconium oxide that is contained in the finished catalyst substrate as at least equal to 50% by weight and often at least equal to 75% by weight relative to the weight of the finished catalyst. The term minority should be understood as defining a proportion of binder in the substrate of the finished catalyst as at most equal to 50% by weight and often at most equal to 25% by weight relative to the weight of the finished catalyst.

When the substrate of the catalyst that is used in the implementation of this invention contains a binder, the latter is usually a mineral binder that is preferably selected from the group that is formed by aluminas, silica, silica-aluminas, clays, magnesia, titanium oxides, boron oxides and combinations thereof.

According to a preferred embodiment of this invention, a shaped catalyst is used that contains:
a substrate that usually develops a specific surface area of 50 to 500 $m^2/g$, preferably 80 to 450 $m^2/g$, a pore volume of 0.2 to 0.9 $cm^3/g$, preferably 0.3 to 0.8 $cm^3/g$, 12-tungstophosphoric acid and/or 12-tungstomolybdic acid. The acid content is usually from 10 to 55% by weight and preferably 25 to 50% by weight relative to the weight of finished catalyst of 12-tungstophosphoric acid and/or 12-tungstomolybdic acid.

This catalyst has remarkable properties for the production of phenylalkanes by alkylation of benzene by means of monoolefins.

To prepare the catalyst that is used for the implementation of this invention, an aqueous solution of the acid or acids is used. They are deposited on substrates by any impregnation technique that is known to one skilled in the art and in particular by dry impregnation in the pore volume. Before impregnation, the substrates are advantageously calcined, for example, at a temperature of about 200° C. to about 800° C., preferably from about 350° C. to about 600° C. After impregnation, the catalyst is dried in an oven for about 6 to 12 hours at a temperature of about 100 to about 150° C., then calcined in air for a period of about 0.5 to about 4 hours, preferably from about 1 to about 3 hours, at a temperature of from about 150° C. to about 400° C., preferably from about 180° C. to about 350° C. At the end of the calcination, in general a treatment under hydrogen is initiated for a period of about 0.5 to about 4 hours, preferably from about 1 to about 3 hours, at a temperature of about 120° C. to about 600° C., preferably from about 150° C. to about 500° C.

The shaping of balls or extrudates can be done by any techniques that are known to one skilled in the art before or after impregnation of the acid or acids.

According to a preferred way of implementing the process of the invention, benzene is reacted in a reaction zone with a feedstock that contains at least one olefin upon contact with a catalyst that has the characteristics that are defined above (alkylation reaction), then the product that is obtained at the end of the alkylation zone is fractionated so as to collect separately a first fraction that contains unconverted benzene, whereby a second fraction contains at least one unconverted olefin, a third fraction contains 2-, 3-, 4-, 5- and 6-phenylalkanes and a fourth fraction contains at least one polyalkylbenzene (or polyalkylbenzene fraction), whereby the latter is then at least in part recycled to said reaction zone where it reacts with benzene upon contact with said catalyst so as to be at least partly transalkylated (transalkylation reaction), and a mixture of 2-, 3-, 4-, 5- and 6-phenylalkanes is collected.

This variant of the invention is therefore characterized in particular by the fact that the alkylation and transalkylation reactions take place together in the same reaction zone (i.e., in the same reactor) in the presence of the same catalyst. In a preferred manner, the first fraction that contains unconverted benzene is at least in part recycled to said reaction zone. Likewise, in a preferred manner, the second fraction that contains at least one unconverted olefin is at least in part recycled to said reaction zone.

According to another variant embodiment of the invention, the product that is obtained at the end of the alkylation zone is fractionated into a first fraction that contains unconverted benzene, a second fraction that contains at least one unconverted olefin, a third fraction that contains 2, 3-, 4-, 5- and 6-phenylalkanes, and a fourth fraction that contains at least one polyalkylbenzene, whereby said fourth fraction is at least in part treated in a second reaction zone, different from the alkylation zone of the benzene that contains the catalyst that comprises 12-tungstophosphoric acid and/or 12-tungstomolybdic acid, deposited on a substrate that develops a large specific surface area and a high pore volume comprising a majority proportion of zirconium oxide ($ZrO_2$), whereby said second reaction zone contains a transalkylation catalyst, for example an EUO-structural-type zeolite such as the one that is described by the applicant in Patent Application FR-A-2,795,402 or any other transalkylation catalyst that is well known to one skilled in the art and is kept under conditions that allow the formation of monoalkylbenzene by reaction between this or these polyalkylbenzene(s) and fresh benzene or that is obtained at least in part from the first fraction that is obtained during the fractionation of the effluent of the mixture that exits from the benzene alkylation zone upon contact with a catalyst that has the characteristics that are defined above. Advantageously, the first fraction that contains unconverted benzene and the second fraction that contains at least one unconverted olefin are recycled at least in part to the alkylation zone.

The portion that is recycled or treated in a transalkylation zone of the fourth fraction that usually contains essentially at least one dialkylbenzene is preferably basically free of heavy alkyl-aromatic compounds that can optionally be eliminated by fractionation.

In the process according to this invention, the alkylation reaction can be carried out at a temperature of between 50 and 300° C., under a pressure of 1 to 10 MPa, with a liquid hydrocarbon flow rate (hourly volumetric flow rate) of about 0.5 to about 50 h$^{-1}$ (volumes per volume of catalyst and per hour) and with a benzene/olefin molar ratio of between 1:1 and 20:1.

In the process of this invention that comprises the implementation of a transalkylation reaction, the latter is usually carried out under a pressure of about 1.5 to about 10 MPa, a temperature of about 100 to about 500° C., an hourly volumetric flow rate of about 0.5 to about 50 h$^{-1}$ and a benzene/polyalkylbenzene molar ratio of about 2:1 to about 50:1.

EXAMPLE 1

49.85 g of 12-tungstophosphoric acid ($H_3PW_{12}O_4$) is dissolved in 30 cm$^3$ of water. This solution is impregnated in the pore volume of 49.85 g of a zirconium oxide substrate that is put in extrudate form (100%) (Vp=0.21 cm$^3$/g; $S_{BET}$=93 m$^2$/g; pore diameter of between 5 and 15 nm). The solid that is thus obtained is then dried for 12 hours in the oven at 120° C. and then calcined for 2 hours at 200° C. under air. It contains 29.8% by weight of 12-tungstophosphoric acid.

The catalyst that is thus prepared is used in alkylation of benzene by dodecene-1.

The following operating conditions are used:
Temperature: 130° C.
Operating pressure: 60 bar
VVH: 1 1/1/h
Benzene/dodecene-1 molar ratio: 4.85 mol/mol Under such conditions, the conversion that is expressed relative to dodecene-1 is 100%. The selectivity of 2 phenylalkane is 31.0% and that of dialkylbenzene is 2.2%.

The preceding examples can be repeated with similar success by substituting the generically or specifically described reactants and/or operating conditions of this invention for those used in the preceding examples.

The entire disclosure of all applications, patents and publications, cited above and below, and of corresponding French Application No. 01/10.622, filed Aug. 8, 2001 is hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for the production of a mixture of compounds comprising at least one 2-, 3-, 4-, 5- or 6-phenylalkane, said process comprising alkylating benzene in a reaction zone with at least one monolefin being at least two carbon atoms, in the presence of catalytic quantity of a finished catalyst comprising at least one of 12-tungstophosphoric acid or 12-tungstomolybdic acid on a substrate, said substrate consisting essentially of zirconium oxide in an amount equal to at least 50% by weight of the finished catalyst and a minor amount of a binder that is alumina, said alkylating being conducted under a pressure of 1 to 10 MPa, a temperature of 50 to 300° C., an hourly volumetric flow rate of about 0.5 to about 50 h$^{-1}$, and a benzene/olefin molar ratio of 1:1 to 20:1.

2. A process according to claim 1, comprising producing a mixture of 2-, 3-, 4-, 5- or 6-phenylalkanes simultaneously.

3. A process according to claim 1, wherein the monoolefin is a linear olefin.

4. A process according to claim 1, wherein the monoolefin is a branched olefin.

5. A process according to claim 1, wherein the monoolefin comprises 9 to 16 carbon atoms in its molecule.

6. A process according to claim 1, wherein the monoolefin comprises 10 to 14 carbon atoms in its molecule.

7. A process according to claim 1, wherein the substrate of the catalyst comprises a majority proportion of zirconium oxide and not more than 25% of said alumina binder.

8. A process according to claim 1, said substrate having a specific surface area of 50 to 500 m$^2$/g and a pore volume of 0.2 to 0.9 cm$^3$/g and said catalyst comprising 10 to 55% by weight of said at least one of 12-tungstophosphoric acid or 12-tungstomolybdic acid.

9. A process according to claim 1, wherein the catalyst is in the form of balls or extrudates.

10. A process according to claim 1, wherein the catalyst has a mechanical resistance sufficient to provide a bed crushing value greater than about 0.7 MPa.

11. A process according to claim 1, further comprising fractionating the resultant mixture of compounds into a first fraction containing unconverted benzene, a second fraction containing at least one unconverted olefin, a third fraction containing 2-, 3-, 4-, 5- or 6-phenylalkanes, and a fourth fraction containing at least one polyalkylbenzene, and recycling at least a part of the said fourth fraction to the alkylation zone.

12. A process according to claim 1, further comprising fractionating the resultant mixture of compounds into a first fraction containing unconverted benzene, a second fraction containing at least one unconverted olefin, a third fraction containing at least one phenylalkane, and a fourth fraction containing at least one polyalkylbenzene, and reacting said fourth fraction at least in part in a transalkylation zone, different from said reaction zone for alkylating benzene, in contact with a transalkylation catalyst under conditions for forming mono-alkylbenzene by reaction between polyalkylbenzene(s) and benzene.

13. A process according to claim 12, wherein the transalkylation zone is under a pressure of about 1.5 to about 10 MPa, a temperature of about 100 to about 500° C., an hourly volumetric flow rate of about 0.5 to about 50 h$^{-1}$, and a benzene/polyalkylbenzene molar ratio of about 2:1 to about 50:1.

14. A process according to claim 11, further comprising recycling the first fraction at least in part to the alkylation zone.

15. A process according to claim 14, further comprising recycling the second fraction at least in part to the alkylation zone.

16. A process according to claim 1, wherein the catalyst comprises 12-tungstophosphoric acid.

17. A process according to claim 1, wherein the catalyst of zirconium oxide in the substrate is equal to at least 75% by weight of the finished catalyst.

18. A process according to claim 16, wherein the catalyst of zirconium oxide in the substrate is equal to at least 75% by weight of the finished catalyst.

19. A process according to claim 18, wherein the monoolefin is a linear olefin.

20. A process according to claim 8, wherein the catalyst of zirconium oxide in the substrate is equal to at least 75% by weight of the finished catalyst.

21. A process according to claim 9, wherein the specific surface is 80–450 m$^2$/g and the pore volume is 0.3–0.8 cm$^3$/g.

* * * * *

UNITED STATES PATENT AND TRADEMARK OFFICE
CERTIFICATE OF CORRECTION

PATENT NO. : 7,098,370 B2  
APPLICATION NO. : 10/214431  
DATED : August 29, 2006  
INVENTOR(S) : Christine Travers Page 1 of 1

It is certified that error appears in the above-identified patent and that said Letters Patent is hereby corrected as shown below:

On the title page, item (75), Inventors: line 2, reads "Jean-Fransois" should read -- Jean-François --
On the title page, Inventors: line 2, reads "Lyons" should read -- Lyon -- Column 8, line 10, reads "according to claim 9," should read -- according to claim 8, --

Signed and Sealed this

Twelfth Day of June, 2007

JON W. DUDAS  
*Director of the United States Patent and Trademark Office*